United States Patent [19]

Lazenby et al.

[11] Patent Number: 5,111,824
[45] Date of Patent: May 12, 1992

[54] COMPOSITE BEAM ULTRASOUND IMAGING SYSTEM HAVING REDUCED IMAGE ARTIFACT

[75] Inventors: John C. Lazenby, Fall City; James Riley, Redmond, both of Wash.

[73] Assignee: Quantum Medical Systems, Incorporated, Issaquah, Wash.

[21] Appl. No.: 561,108

[22] Filed: Aug. 1, 1990

[51] Int. Cl.⁵ .................... A61B 8/00; G01N 29/04
[52] U.S. Cl. .................... 128/661.01; 73/626; 73/631
[58] Field of Search .......... 128/660.01, 660.02, 128/660.07, 661.01; 73/602, 625, 626, 631

[56] References Cited

U.S. PATENT DOCUMENTS

| | | | |
|---|---|---|---|
| 4,398,539 | 8/1983 | Proudian | 73/626 X |
| 4,665,924 | 5/1987 | Saito et al. | 128/661.01 |
| 4,691,570 | 9/1987 | Hassler | 73/626 |
| 4,707,813 | 11/1987 | Moeller et al. | 73/626 X |
| 4,779,622 | 10/1988 | Nakamura et al. | 73/626 X |
| 4,813,279 | 3/1989 | Shirosaka et al. | 73/626 |
| 4,974,558 | 12/1990 | Katakura et al. | 128/661.01 |

FOREIGN PATENT DOCUMENTS 2045435 10/1980 United Kingdom ............. 73/626

Primary Examiner—Francis Jaworski
Attorney, Agent, or Firm—Lawrence C. Edelman

[57] ABSTRACT

An apparatus for electrically blending echoes from a plurality of focused beams into a composite image having reduced image artifacts. The apparatus comprises a transducer generating a sequence of beams having different focal points and converting resultant echoes into electrical signals, a receiver with its gain adjusted according to (1) time and (2) the transmitted beam, a multiplier that develops the product of the receiver output and a gain selected both by the transmitted beam and (time), and a summing network that adds together outputs of the multiplier that originated from the same sound scatterer.

19 Claims, 5 Drawing Sheets

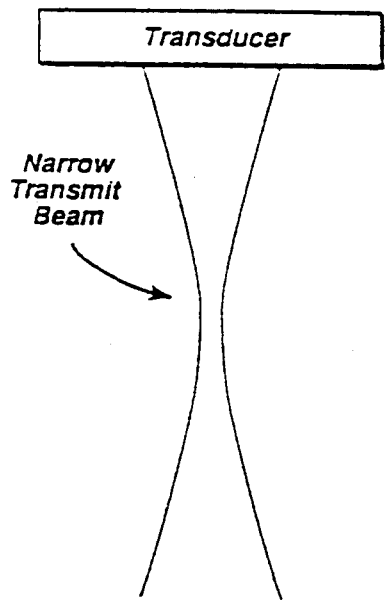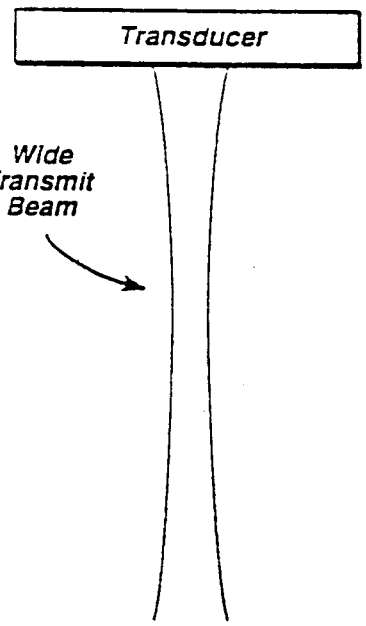
*Figure 2A*  *Figure 2B*
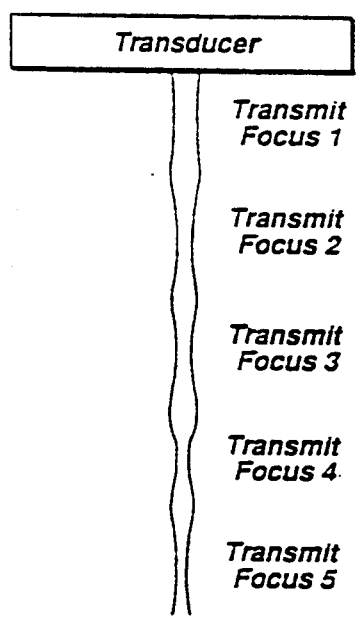
*Figure 3*

COMPOSITE BEAM ULTRASOUND IMAGING SYSTEM HAVING REDUCED IMAGE ARTIFACT

TECHNICAL FIELD

This invention relates to ultrasonic imaging. In particular, this invention relates to electronically blending echoes from a plurality of separately focused ultrasonic beams to produce a composite image having reduced image artifacts.

BACKGROUND OF THE INVENTION

Ultrasonic imaging has proved useful in the medical arts because of its ability to provide structural information about a patient's subcutaneous sound scatterers (organs, blood, bones, etc.). Typically, ultrasonic imaging systems (1) transmit ultrasonic energy from a transducer through a patient's skin, (2) electrically process echoes from the patient's subcutaneous sound scatterers, and (3) produce an image of those sound scatterers on a display device. It is highly desirable to increase the image detail so that improved analysis of the sound scatterers is possible. However, before increased image detail can be achieved, the structural information from the sound scatterers must be increased.

One method of increasing the structural information is to focus the transmitted ultrasonic energy into a small cross-sectional area. Focused ultrasonic energy, hereinafter referred to as a beam, increases the structural information by increasing the energy applied to sound scatterers near the beam's focal point while reducing the energy applied to adjacent tissues, thereby providing increased echo discrimination. However, as is well known to those in the art, a focused beam has its ultrasonic energy contained in a beam profile that widens as the distance from the beam's focal point increases. Therefore, at locations remote from the beam's focal point, the advantages of focusing are lost since the beam's cross-sectional area necessarily increases.

Some conventional ultrasound imaging systems have sought to overcome focusing limitations by combining echoes from multiple beams, each having a different focal length, to form a composite image. While systems using multiple beams have proved successful, the combining of the echoes typically produces undesirable bright or dark lines, called image artifacts, in interstitial areas between the beam's focal points.

Therefore, it is clear that there has existed a need for a system that smoothly blends echoes resulting from a plurality of beams having different focal points to form a composite image having reduced image artifacts.

SUMMARY OF THE INVENTION

It is an object of the present invention to provide a system that blends echoes from a plurality of beams focused at different points so that the derived structural information could be displayed with reduced image artifacts.

This and other objects of this invention are accomplished by generating a sequence of beams having different focal points; converting any resulting echoes into electrical signals; amplifying the electrical signals by a time variable gain dependant on the beam's beam profile; producing for each beam a sequence of sampled received signals from the amplified electrical signals; and blending the sampled received signals to form a composite image.

In the preferred embodiment, the blending of the sampled received signals to form the composite image includes temporarily storing the sampled received signals, multiplying each sampled received signal by a gain coefficient determined by (1) the beam that caused the sampled received signal and (2) the location of the sound scatterer that caused the sampled received signal, and summing the gain multiplied received signals to form a composite image.

BRIEF DESCRIPTION OF THE DRAWINGS

FIGS. 2A and 2B are schematics illustrating the trade-off between narrowness of focus and depth of field in conventional ultrasound imaging systems.

FIG. 3 is a schematic illustrating the manner in which multiple beams can be combined to generate a narrowly focused beam over a wide depth of field.

DETAILED DESCRIPTION OF THE INVENTION

Figure 1A:
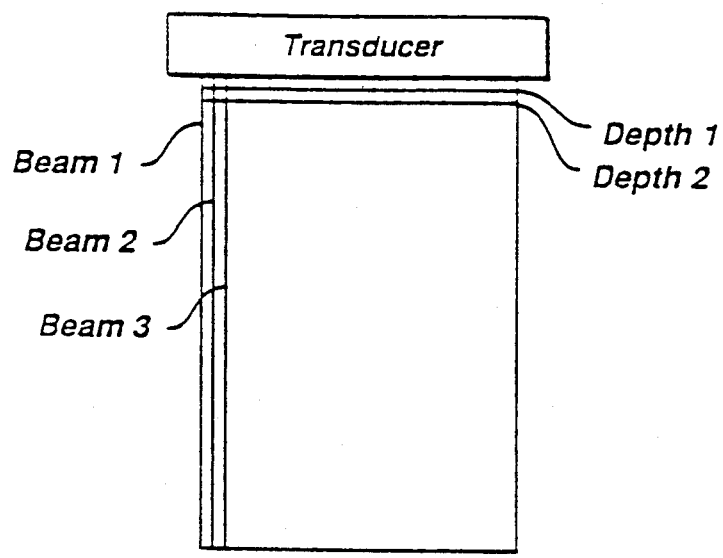
FIG. 1A and 1B are schematics illustrating the formation of raster scan and sector scan images, respectively.

Conventional ultrasound imaging systems generally operate in two distinct scan modes. In a raster scan, as illustrated in FIG. 1A, an ultrasound transducer is placed against the skin of a patient. The ultrasound transducer includes a large number of transducer elements, each of which generates a pulse of ultrasound energy upon receipt of an ultrasound transmit signal. The transducer elements also each generate an electrical receiver signal when they detect ultrasound returns reflected from tissue scatterers in the patient.

The transducer elements, either alone or in groups of adjacent elements, implement a series of ultrasound beams, each of which detects tissue scatterers in the volume beneath the element(s) forming the beam. Thus, in the example illustrated in FIG. 1A, the leftmost transducer element or group of adjacent elements forms beam 1 while the next transducer element or group of adjacent elements forms beam 2. The rightmost transducer element or group of adjacent elements forms beam M. In the event that the beams are formed by respective groups of elements, the beams may overlap so that a given transducer element may be used as part of two different beams. As is well understood in the art, the use of multiple transducer elements to form beams allows the beam to be focused to a particular depth.

In a raster scan, as illustrated in FIG. 1A, the beams are active in sequence so that each beam examines a volume extending from the transducer into the patient. The resulting image obtained by a raster scan generally simulates a cross section through the tissue of a patient.

Figure 1B:
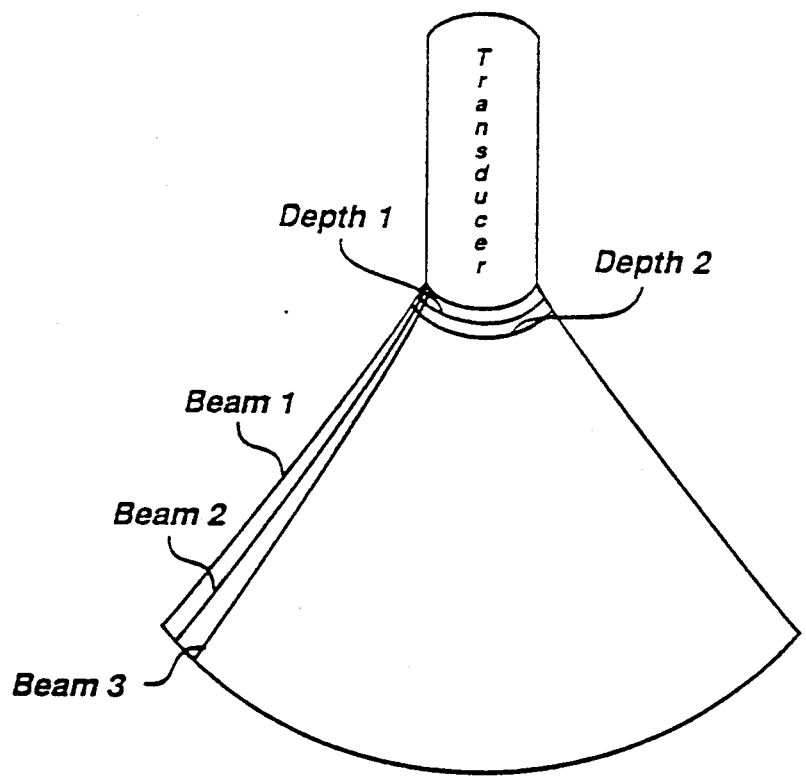

A sector scan, as illustrated in FIG. 1B, is also composed of multiple beams, each of which may be formed by a single element or several adjacent elements of an ultrasound transducer. However, unlike the raster scan beams (which extend into the patient in parallel with each other), the sector scan beams essentially emanate from a point and extend into the patient at varying angles. The inventive imaging system can be advantageously used with either a raster scan or a sector scan imaging system.

The returned signal for each beam position is sampled at discrete intervals which correspond to discrete depths in the image. As illustrated in FIG. 1, the shallowest sample depth is depth 1, the next shallowest sample depth is depth 2, and so on. The sampling process is essentially the same for both raster scans and sector scans.

If an ultrasound beam is formed using multiple transducer elements, then for each transmit pulse the ultrasound energy may be focused at a particular depth. In single transmit focus mode only one transmit pulse is needed per beam and the ultrasound energy may either be focused to form a narrow beam over a small range of depth as illustrated in FIG. 2A, or to form a wider beam over a larger range of depth as illustrated in FIG. 2B. A narrow ultrasound beam allows smaller details to be resolved in the ultrasound image, so it is desirable to have an ultrasound beam which is narrow over as large a depth range as possible.

With reference to FIG. 3, a multiple transmit focus beam is formed by combining the signals from several transmit pulses. Each of those transmit pulses is focused to a narrow beam, and each is focused to a different depth. By combining that part of each pulse where the transmitted ultrasound beam is narrowest into a multiple transmit focus beam, the resultant multiple transmit focus beam will be narrow over a large depth range. The process of combining several transmit pulses into a multiple transmit focus beam will be referred to as zone blending.

The idea of zone blending is to ensure that at each depth of each beam the contribution to the multiple transmit focus beam is greatest from the transmit pulse whose focal point is closest to that depth. However, it is beneficial to include some contribution from the other transmit pulses in order to make the transitions as smooth as possible, and also in order to produce a pleasing texture in the output image. Therefore, the degree to which the various transmit pulses contribute to the multiple focus transmit beam must be widely adjustable and it must be specifiable as a function of depth.

Figure 4:
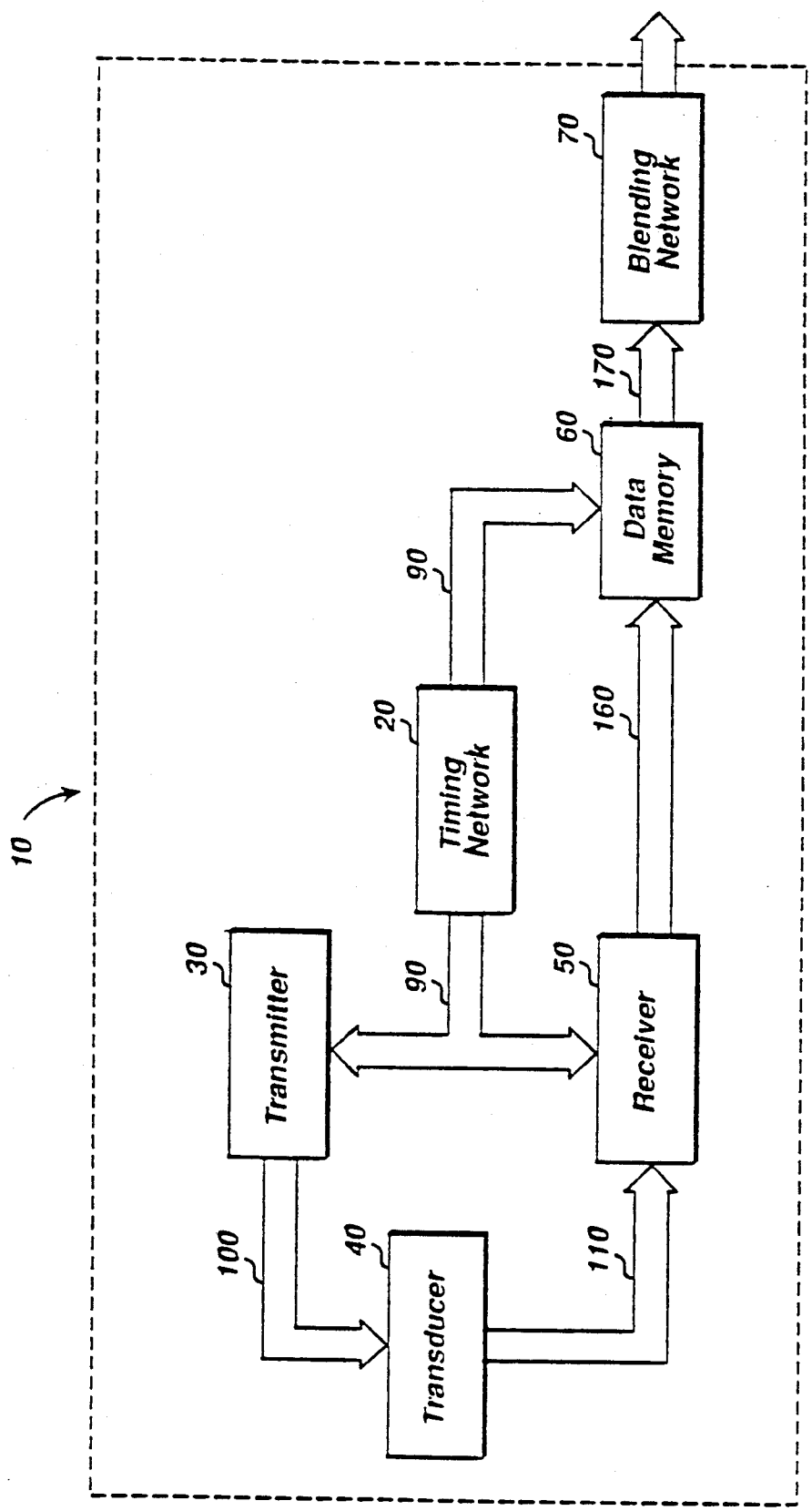
FIG. 4 is a block diagram illustrating the preferred embodiment of the present invention.

A functional block diagram of a zone blender 10 according to the preferred embodiment is shown in FIG. 4. The zone blender 10 includes a timing network 20, a transmitter 30, a transducer 40, a receiver 50, a data memory network 60, and a blending network 70. The operation of these sections is described in detail below.

For proper operation, the zone blender 10 requires that its sections operate at precise times and in an exact order. In the preferred embodiment, synchronization is achieved via the timing network 20. The timing network 20 generates a programmed sequence of digital words on a digital word line 90 at precise times. These digital words are decoded and used by the other sections to synchronize their operations. Specifically, digital words from the timing network 20 prompts (1) the transmitter 30 to produce specific beams from the transducer 40, (2) the receiver 50 to adjust its gain and reset its timing, and (3) the data memory network 60 to determine that the programmed sequence is complete. Further discussions of how each section uses the digital words are provided in the descriptions that follow. While the preferred embodiment uses random access memory (RAM) loaded by a computer to generate the digital words, those skilled in the art can implement the function of the timing network 20 by using other well-known circuit designs, such as those based on programmable read-only memories (PROMS) or sequential counters.

According to the present invention, an ultrasonic transducer generates a plurality of separately focused beams each having a focal point at a different depth. This can be accomplished because ultrasonic transducers can be constructed using individual transducing elements excitable so that their composite outputs form focused beams. When the excitations change, the focal point of the resulting beam changes. These operations are well known to those skilled in the art.

In the preferred embodiment, the transducer 40 is constructed with individual elements, as above. The individual elements connect to the transmitter 30 via individual lines of a transmitter output bus 100. The beam to be generated is set by the digital word applied to the transmitter 30 on digital word bus 90. To form a given beam, the transmitter 30 decodes the digital word, selects the lines of the transmitter output bus 100 to be excited, and the excitation's timing. When the digital word changes, the transmitter decodes the new word, selects new elements and timing, and generates another beam. Therefore, by varying the digital word, the focal point of the transmitted energy can be caused to increment from a shallow tissue depth to deeper tissue depths. The digital words, the transmitter output bus 100, the number and layout of the individual transducing elements within the transducer 40, and the timing and decoding functions of the transmitter 30 all must be implement as part of a common scheme. However, those skilled in the art will be able to implement this scheme. Indeed, the above requirements are identical to those of prior art multiple ultrasonic beam imaging systems that form composite images.

During operation, the beams from the transducer 40 are transmitted into a patient's subcutaneous tissue. The beams travel through the tissue until they collide with a sound scatterer, such as a vein, a bone, or the interface between tissue layers. Collisions cause echoes that reflect back to the transducer 40, which converts the echoes into electrical signals. These electrical signals are applied to the receiver 50 via a receiver input bus 110. Preferably, each individual transducing element of transducer 40 connects with the receiver 50.

Figure 5:
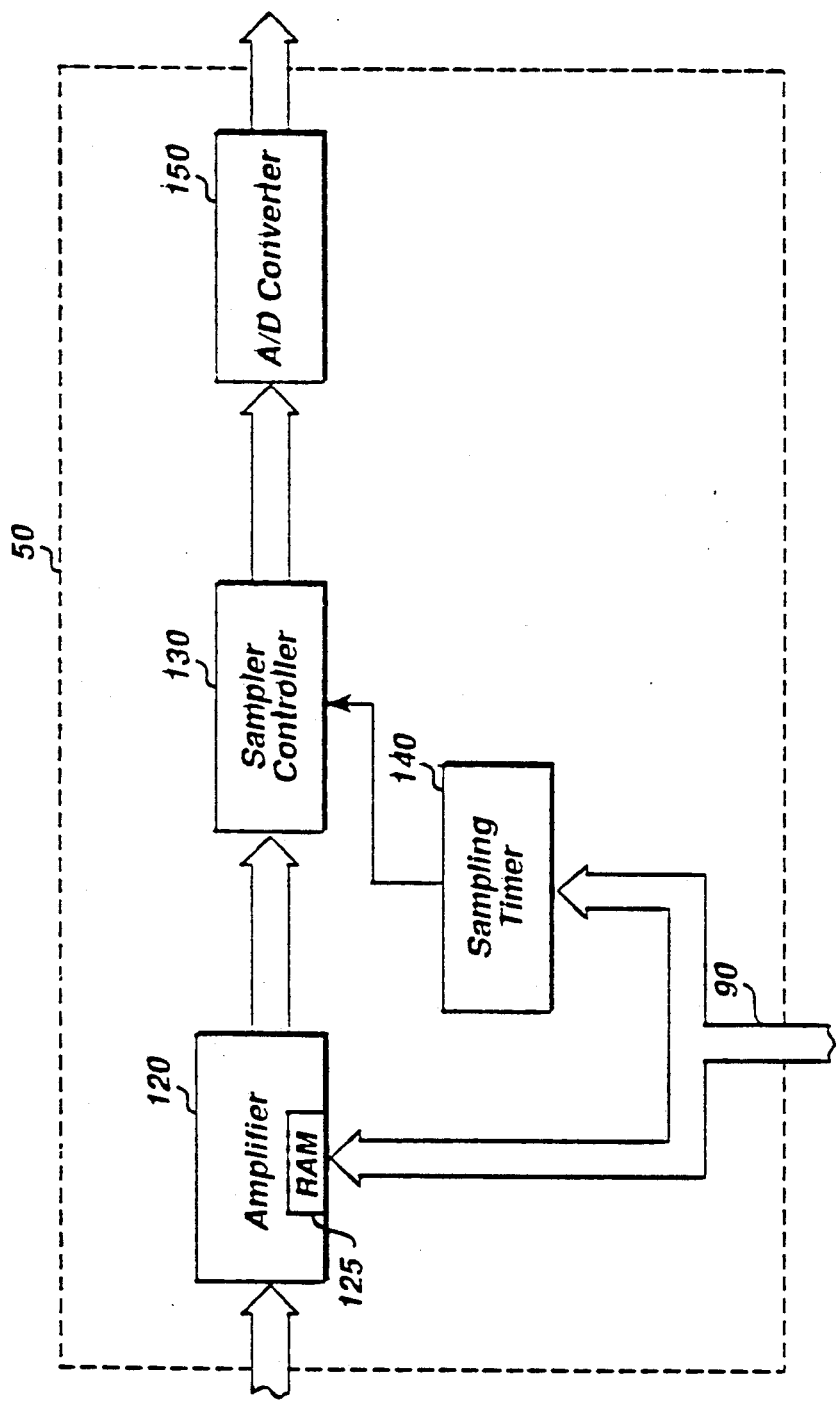
FIG. 5 is a block diagram of a receiver used in the preferred embodiment of FIG. 4.

The receiver 50, as shown in FIG. 5, includes an amplifier 120, a sampler controller 130, a sampling timer 140, and an A-to-D converter 150. The amplifier 120 receives the electrical signals on the receiver input bus 110 and amplifies them to levels usable by the A-to-D converter 150. In the present invention, the amplification of these electrical signals varies not only as a function of time, as in prior art systems, but also as a function of the particular beam being generated. This beam dependency compensates for the spreading of each beam's beam profile as a function of distance from that beam's focal point. Therefore, each beam from the transducer must have its own separate amplification curve.

In the preferred embodiment, the amplification curve for each beam is stored inside a random access memory (RAM) 125 inside the amplifier 120. The digital word applied on the digital word bus 90 is used as an address for the RAM 125, which, in turn, outputs a unique digital pattern that controls the amplification curve of the amplifier 120.

The amplification curves can be calculated for each beam's beam profile or they can be determined by experimentation. These amplification curves are chosen to cause the same amplitude output from the receiver 120 for (1) an arbitrary sound scatterer at different distance from the transducer and (2) the same sound scatter for different beams. The first requirement implement the typical time variable gain function used in prior art ultrasonic imaging systems receivers. The second requirement compensates for the transmitted beam's beam profile. While determination of the amplification curves are tedious, they are straight forward and the methods are well known to those skilled in the art.

The output of the amplifier 120 is applied to a sampler controller 130, which is controlled by a sampling timer 140. The sampler controller 130 passes information from the amplifier 120 to the A-to-D converter 150 when, and only when, gated by the sampling timer 140. Therefore, sampling timer 140 controls when outputs from the receiver 50 occur. The purpose of the sampling timer 140 is to create sampled receiver outputs corresponding to echoes from fixed distances from the transducer 40. This allows the zone blender 10 to "fit" echoes from the same sound scatterer, but caused by different beams, together. The zone blender 10 uses the relationship between speed (S), distance (D), and time (T), $D = S*T$, to determine that echoes from different beams are from the same sound scatterer. Since the speed of ultrasonic energy in tissue is relatively constant, the distance from the transducer is a direct function of time, which can be accurately set using well known circuit designs. By gating the sampler controller 130 at fixed times, measured from the start of each beam, the same locations are sampled for each beam.

In the preferred embodiment, when the digital word on the digital word bus 90 changes, a plurality of equally spaced gating signals from the sampling timer 140 are applied to the sampler controller 130, causing the same location to be scanned for each beam. These gating signals occur at a sufficiently high rate so that the information obtained approximates that which would be obtained from continuous monitoring.

The output of the sampler controller 130 is applied to the A-to-D converter 150 for conversion from analog to digital singals. The A-to-D converter 150 outputs a series of digital words that represent the magnitudes of the outputs of the amplifier 120 at the sampling times. The outputs take the form:

---
Echo magnitude at distance 1 for Beam 1
Echo magnitude at distance 2 for Beam 1
.
.
.
Echo magnitude at distance N for Beam 1
Echo magnitude at distance 1 for Beam 2
Echo magnitude at distance 2 for Beam 2
.
.
.
Echo magnitude at distance N for Beam 2
Echo magnitude at distance 1 for Beam X
Echo magnitude at distance 2 for Beam X
.
.
.
Echo magnitude at distance N for Beam X
--- where N is the number of samples taken per beam and X is the number of beams.

Those skilled in the art will be familiar with numerous circuit designs suitable for implementing the functions of the receiver 50. Indeed, except for using time variable gains dependent on digital words, the receiver 50 is similar to, or identical with, prior art receiver designs.

Referring again to FIG. 4, the output of the receiver 50 is applied via receiver output line 160 to the data memory network 60, which also connects to the digital word bus 90. The data memory network 60 stores the sampled outputs from the receiver 50 together with the digital word that represents the beam that caused those outputs. In the preferred embodiment, the data memory network 60 is a random access memory (RAM) having sufficient appropriately sized registers to store all of the outputs from the receiver 50 together with their associated digital words. The data memory network 60 accumulates this information until the last sampled output of the receiver 50 associated with the last digital word in the programmed sequence occurs. The data memory network 60 then downloads its stored data to the blending network 70 via a data output bus 170.

Figure 6:
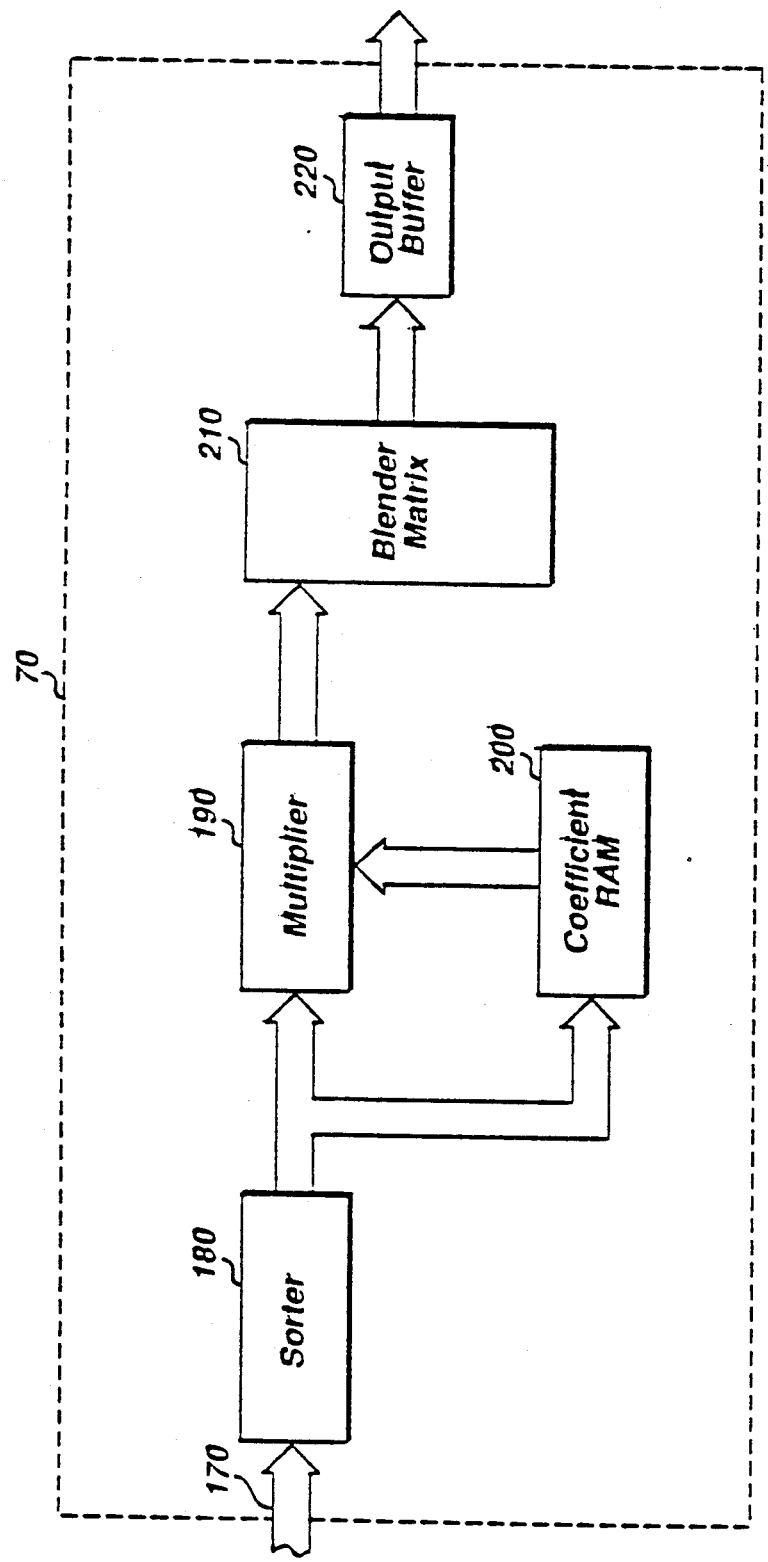
FIG. 6 is a block diagram of a blending network used in the preferred embodiment of FIG. 4.

The blending network 70 shown in FIG. 6 includes a sorter 180, a multiplier 190, a coefficient random access memory 200, a blender matrix 210 and an output buffer 220. When the data memory network 60 downloads its stored data, that data is temporarily stored in, and processed by, the sorter 180. The sorter 180 sorts the downloaded data so that it is ordered by the location of the sound scatterer that caused it and, for each location, by the digital word that caused it. The sorter 180 sorts the measurements to the form:

---
Echo magnitude at distance 1 for Beam 1
Echo magnitude at distance 1 for Beam 2
Echo magnitude at distance 1 for Beam 3
.
.
.
Echo magnitude at distance 1 for Beam X
Echo magnitude at distance 2 for Beam 1
Echo magnitude at distance 2 for Beam 2
Echo magnitude at distance 2 for Beam 3
.
.
.
Echo magnitude at distance 2 for Beam X
.
.
.
Echo magnitude at distance N for Beam 1
Echo magnitude at distance N for Beam 2
Echo magnitude at distance N for Beam 3
.
.
.
Echo magnitude at distance N for Beam X
--- where N and X are as given previously. The sorted data is then applied to both the multiplier 190 and to the coefficient RAM 200. The operation of the sorter 180 is well known to those skilled in the art and its functions can be implemented using well known circuit design techniques.

According to the present invention, echo blending requires (1) that the magnitude of each echo be scaled according to its importance in developing the composite image and (2) that the scaled magnitudes at each distance be summed together to create the composite image. The multiplier 190 performs the scaling functions by multiplying the magnitude of the sorted data from the sorter 180 by a predetermined gain coefficient stored in the coefficient RAM 200, and then applies the result to the blender matrix 210 for summing.

Consider a system having five (5) beams spanning an arbitrary distance. Beam one (1) is focused at 10% of the arbitrary distance, beam two (2) at 30%, beam three at 50% and so on. Near each beam's focal point the "importance" of echoes from that beam to the composite image are one (1), indicating that the composite image at that distance is derived solely from the beam focused there. However, as the distance from each beam's focal point increases, the importance of echoes resulting from that beam decreases. For example, the importance of beam 1 might drop to zero at about 27% of the arbitrary distance. However, in interstitial locations, the importance of echoes from two beams must be considered. For example, at a distance of 20% of the maximum, the importance of beam 1 might be 0.5 and the importance of beam 2 might also be 0.5. Therefore, the magnitude of echoes from beams 1 and 2 should be multiplied by 0.5, and then added together.

As indicated, the gain coefficient for each sampled received signal is stored in the coefficient RAM 200. These gains are selected according to the importance each sampled received signal has to the composite image. The coefficient RAM 200 uses the sampled received signal's location (distance) and digital word (beam) as addresses, selects the gain coefficient stored at that address, and outputs the selected gain to the multiplier 190. The multiplier 190 then performs the multiplication previously discussed. Thus the scaled signals going to the blender matrix 210 appear as:

---
Scaled magnitude of echo from distance 1 for Beam 1
Scaled magnitude of echo from distance 1 for Beam 2
Scaled magnitude of echo from distance 1 for Beam 3
.
.
.
Scaled magnitude of echo from distance 1 for Beam X
Scaled magnitude of echo from distance 2 for Beam 1
Scaled magnitude of echo from distance 2 for Beam 2
Scaled magnitude of echo from distance 2 for Beam 3
.
.
.
Scaled magnitude of echo from distance 2 for Beam X
.
.
.
Scaled magnitude of echo from distance N for Beam 1
Scaled magnitude of echo from distance N for Beam 2
Scaled magnitude of echo from distance N for Beam 3
.
.
.
Scaled magnitude of echo from distance N for Beam X
---

In the preferred embodiment, the gain coefficients are predetermined for the proper "fit" and are loaded by a microprocessor during circuit initialization. The gains themselves can be determined by experimentation to give the desired smoothness. However, the "importance" of adjacent beams in the preferred embodiment is as previously discussed, except the number of separate beams is 48. Those skilled in the art can easily implement the functions of the coefficient RAM 200 and the multiplier 190 using well known design techniques.

As indicated, the scaled signals from multiplier 190 are summed into a composite image by the blender matrix 210. Since the preferred embodiment has used the sorter 180 to sort the sampled received signals, the inputs to the blender matrix 210 are conveniently arranged by location. The blender matrix 210 adds the scaled signals for each location together to develop composite distance signals, which are applied to the output buffer 220, which stores each composite distance signal in a separate memory register. This results in a complete composite image accessible in the output buffer 220 by locations. In addition to storing the composite image, the output buffer 220 acts as an interface to the external circuitry. While the composite image will typically be scanned by a display device, other uses may be made of the composite image. Those skilled in the art can easily implement the functions of the output buffer 220 using well known circuit designs.

While the preferred embodiment of a zone blender 10 is described above, numerous modifications are possible. For example, the sorter 180 can be eliminated in alternate designs, or the functions of the sorter 180 and the data memory network 60 could be combined. Therefore, the preferred embodiment is illustrative only and numerous changes can be made within the principles of the present invention.

What is claimed is:

1. A system for blending data obtained from a plurality of ultrasound returns generated from ultrasound beams focused at different tissue depths to simulate an ultrasound beam having a relatively narrow focus over a wide depth of field, comprising:
   memory means for storing a plurality of coefficients each of which is a function of the distance between the tissue depth at which each ultrasound beam is focused and the depth of each ultrasound return in said beam so that returns from tissue depths that are closer to the tissue depth at which an ultrasound beam is focused have a larger coefficient than returns from tissue depths that are farther from the tissue depth at which said ultrasound beam is focused;
   multiplication means receiving said coefficients from said memory means for multiplying data from each ultrasound return by a coefficient corresponding to the depth of said ultrasound return and the tissue depth at which the ultrasound beam generating said ultrasound return is focused, said multiplication means generating adjusted ultrasound return data from products of ultrasound returns and corresponding coefficients; and
   accumulator means receiving said adjusted ultrasound returned data from said multiplication means, said accumulator means summing adjusted ultrasound return data for a plurality of tissue depths from at least two ultrasound beams thereby simulating an ultrasound beam having a relatively narrow focus over a wide depth of field.

2. The data blending system of claim 1 further including normalization means for multiplying the sum of adjusted ultrasound return data by a normalization factor so that the magnitude of the sum of the adjusted ultrasound return data for each tissue depth is substantially equal to the magnitude that the ultrasound return data from that same tissue depth would have if the ultrasound beam generating such ultrasound return was focused at such depth.

3. The data blending system of claim 1 further including means for multiplying data from each ultrasound return by a gain factor prior to being applied to said multiplier means, each of said gain factors being an inverse function of the depth of said ultrasound return so that ultrasound returns from sound scatterers having the same characteristics at different depths have the same magnitude.

4. The data blending system of claim 3 wherein said gain factor is also a function of the characteristics of said beam.

5. The data blending system of claim 1 wherein said accumulator means sums adjusted ultrasound return data for a plurality of tissue depths from at least two ultrasound beams only if the distance between the tissue depth at which each ultrasound beam is focused and the depth of each ultrasound return in said beam is less than a predetermined value whereby blending of returns from a plurality of ultrasound beams occurs primarily at tissue depths that are spaced from tissue depths at which ultrasound beams are focused.

6. The data blending system of claim 5 wherein said accumulator means sums adjusted ultrasound return data only from ultrasound beams having focus depths that are positioned adjacent each other.

7. An ultrasound imaging system for generating an ultrasound beam having a relatively narrow focus over a wide depth of field, comprising:
an ultrasound transducer having a plurality of transducer elements each of which can be separately transmit and receive ultrasound energy;
a transmitter selectively applying transmit signals to the transducer elements of said ultrasound transducer;
a receiver selectively receiving signals from the transducer elements of said ultrasound transducer, said receiver generating output signals indicative of the amplitude and depth of echoes from sound scatterers in tissue beneath said ultrasound transducer, the output signals from sound scatterers in predetermined ranges of tissue depth being generated in respective beams of ultrasound each of which is focused at a different depth;
first memory means for storing ultrasound return data corresponding to the output signals generated from a range of tissue depths during a plurality of ultrasound beams;
second memory means for storing a plurality of coefficients each of which is a function of the distance between the tissue depth at which each ultrasound beam is focused and the depth of each ultrasound return in said beam so that returns from tissue depths that are closer to the tissue depth at which an ultrasound beam is focused have a larger coefficient than returns from tissue depths that are farther from the tissue depth at which said ultrasound beam is focused;
multiplication means receiving said coefficients from said second memory means for multiplying data from each ultrasound return by a coefficient corresponding to the depth of said ultrasound return and the tissue depth at which the ultrasound beam generating said ultrasound return is focused, said multiplication means generating adjusted ultrasound return data from products of ultrasound returns and corresponding coefficients; and
accumulator means receiving said adjusted ultrasound return data from said multiplication means, said accumulator means summing adjusted ultrasound return data for a plurality of tissue depths from at least two ultrasound beams thereby simulating an ultrasound beam having a relatively narrow focus over a wide depth of field.

8. The ultrasound imaging system of claim 7 further including normalization means for multiplying the sum of adjusted ultrasound return data by a normalization factor so that the magnitude of the sum of the adjusted ultrasound return data for each tissue depth is substantially equal to the magnitude that the ultrasound return data from that same tissue depth would have if the ultrasound beam generating such ultrasound return was focused at such depth.

9. The ultrasound imaging system of claim 7 wherein said receiver further includes means for multiplying data from each ultrasound return by a gain factor, each of said gain factors being an inverse function of the depth of said ultrasound return so that ultrasound returns from sound scatterers having the same characteristics at different depths have the same magnitude.

10. The ultrasound imaging system of claim 9 wherein said gain factor is also a function of the characteristics of said beam.

11. The ultrasound imaging system of claim 7 wherein said accumulator means sums adjusted ultrasound return data for a plurality of tissue depths from at least two ultrasound beams only if the distance between the tissue depth at which each ultrasound beam is focused and the depth of each ultrasound return in said beam is less than a predetermined value whereby blending of returns from a plurality of ultrasound beams occurs primarily at tissue depths that are spaced from tissue depths at which ultrasound beams are focused.

12. The ultrasound imaging system of claim 11 wherein said accumulator means sums adjusted ultrasound return data only from ultrasound beams having focus depths that are positioned adjacent each other.

13. The ultrasound imaging system of claim 7 wherein said transmitter adjusts the phase of transmit signals applied to the transducer elements of said ultrasound transducer thereby focusing the ultrasound beam generated by said ultrasound transducer to a predetermined tissue depth.

14. The ultrasound imaging system of claim 7 wherein said receiver adjusts the phase of output signals received from the transducer elements of said ultrasound transducer thereby focusing the ultrasound beam received by said ultrasound transducer to a predetermined tissue depth.

15. A method of blending data obtained from a plurality of ultrasound returns generated from ultrasound beams focused at different tissue depths to simulate an ultrasound beam having a relatively narrow focus over a wide depth of field, said method comprising:
multiplying data from each ultrasound return by a coefficient corresponding to the distance between the tissue depth at which each ultrasound beam is focused and the depth of each ultrasound return in said beam, said multiplication means generating adjusted ultrasound return data from products of ultrasound returns and corresponding coefficients; and
summing adjusted ultrasound return data for a plurality of tissue depths from at least two ultrasound beams thereby simulating an ultrasound beam having a relatively narrow focus over a wide depth of field.

16. The method of claim 15 further including the step of multiplying the sum of adjusted ultrasound return data by a normalization factor so that the magnitude of the sum of the adjusted ultrasound return data for each tissue depth is substantially equal to the magnitude that the ultrasound return data from that same tissue depth would have if the ultrasound beam generating such ultrasound return was focused at such depth.

17. The method of claim 15 further including the step of multiplying data from each ultrasound return by a gain factor that is an inverse function of the depth of said ultrasound return so that ultrasound returns from sound scatterers having the same characteristics at different depths have the same magnitude.

18. The method of claim 15 wherein adjusted ultrasound return data is summed for a plurality of tissue depths from at least two ultrasound beams only if the distance between the tissue depth at which each ultrasound beam is focused and the depth of each ultrasound return in said beam is less than a predetermined value whereby blending of returns from a plurality of ultrasound beams occurs primarily at tissue depths that are spaced from tissue depths at which ultrasound beams are focused.

19. The method of claim 18 wherein adjusted ultrasound return data are summed only from ultrasound beams having focus depths that are positioned adjacent each other.

* * * * *